(12) United States Patent
Morris et al.

(10) Patent No.: US 8,438,900 B2
(45) Date of Patent: May 14, 2013

(54) ELECTRONIC PHANTOM AND METHOD FOR ELECTRONICALLY CONTROLLING A PHANTOM FOR A QUANTITATIVE ULTRASOUND DEVICE

(75) Inventors: Richard Franklin Morris, Edgerton, WI (US); Steven Taylor Morris, Indianapolis, IN (US)

(73) Assignee: General Electric Company, Schenectady, NY (US)

( * ) Notice: Subject to any disclaimer, the term of this patent is extended or adjusted under 35 U.S.C. 154(b) by 622 days.

(21) Appl. No.: 12/570,583

(22) Filed: Sep. 30, 2009

(65) Prior Publication Data
US 2011/0076659 A1  Mar. 31, 2011

(51) Int. Cl.
*G09B 23/28* (2006.01)

(52) U.S. Cl.
USPC .......................................... 73/1.82; 434/267

(58) Field of Classification Search ..... 434/267; 73/1.82
See application file for complete search history.

(56) References Cited

U.S. PATENT DOCUMENTS

| | | | |
|---|---|---|---|
| 4,286,455 A | | 9/1981 | Ophir et al. |
| 5,625,137 A | | 4/1997 | Madsen et al. |
| 5,649,538 A | * | 7/1997 | Langton ........................ 600/437 |
| 5,670,719 A | | 9/1997 | Madsen et al. |
| 5,755,228 A | | 5/1998 | Wilson et al. |
| 6,264,607 B1 | | 7/2001 | Goll et al. |
| 6,318,146 B1 | | 11/2001 | Madsen et al. |
| 6,352,512 B1 | * | 3/2002 | Wilson et al. ................. 600/449 |
| 6,635,486 B2 | | 10/2003 | Madsen et al. |
| 2004/0243003 A1 | * | 12/2004 | Pasternak et al. ............. 600/449 |
| 2005/0075571 A1 | * | 4/2005 | Barnes .......................... 600/459 |
| 2005/0141672 A1 | * | 6/2005 | Endo et al. .................... 378/207 |
| 2006/0079773 A1 | * | 4/2006 | Mourad et al. ................ 600/438 |

OTHER PUBLICATIONS

Clarke et al, A Phantom for Quantitative Ultrasound of Trabecular Bone, Phys. Med. Biol. 1677-1687 (1991).
Goldstein et al, Ethylene Glycol-Water Mixtures for use in Ultrasound Test Objects, J Clin. Ultrasound 7:465-470 (Dec. 1979).
Corsaro et al, A filled Silicone Rubber Materials System with Selectable Acoustic Properties for Molding and Coating Applications at Ultrasonic Frequencies, NRL Report 8301 (1979).
Ji, A Physical Model for Broadband Ultrasonic Studies of Cancellous Bone, PhD Thesis, University of Alberta (1998).

* cited by examiner

*Primary Examiner* — Hezron E Williams
*Assistant Examiner* — Gregory J Redmann
(74) *Attorney, Agent, or Firm* — Rathe Lindenbaum LLP

(57) ABSTRACT

An electronic phantom and method for electronically controlling a phantom for a quantitative ultrasound device are provided. The electronic phantom includes a housing, a first transducer element within the housing configured to receive an ultrasonic signal from a quantitative ultrasound device and a second transducer element within the housing connected to the first transducer element. The second transducer element is configured to transmit a modified ultrasonic sound wave to the quantitative ultrasound device based on the received ultrasonic signal. The first and second transducer elements are positioned in a back to back configuration within the housing.

11 Claims, 4 Drawing Sheets

| SIMULATED BONE QUALITY | MODULATION CHARACTERISTICS ||
|---|---|---|
| | TIME-OF-FLIGHT | BROADBAND ULTRASOUND ATTENUATION |
| BONE QUALITY A | PROFILE A | PROFILE A |
| BONE QUALITY B | PROFILE B | PROFILE B |
| BONE QUALITY C | PROFILE C | PROFILE C |
| BONE QUALITY D | PROFILE D | PROFILE D |
| BONE QUALITY E | PROFILE E | PROFILE E |
| BONE QUALITY F | PROFILE F | PROFILE F |
| BONE QUALITY G | PROFILE G | PROFILE G |

ELECTRONIC PHANTOM AND METHOD FOR ELECTRONICALLY CONTROLLING A PHANTOM FOR A QUANTITATIVE ULTRASOUND DEVICE

BACKGROUND OF THE INVENTION

The subject matter disclosed herein relates generally to medical diagnostic systems, and more particularly to quantitative ultrasound (QUS) devices.

QUS devices such as ultrasonic densitometers and ultrasonometers use ultrasonic sound waves to measure bone integrity. Validation of QUS devices is an important function to ensure continued proper measurements that allow for proper diagnosis. QUS devices must remain stable for many years in order to properly assess the advancement of osteoporosis or monitor therapies. Thus, measurement parameters such as speed of sound (SOS), also referred to as time-of-flight, and broadband ultrasonic attenuation (BUA) need to be properly measured over time.

QUS phantoms are used to monitor QUS device stability. Conventional QUS phantoms use stable and well-characterized liquids such as water to attenuate signals. Other conventional QUS phantoms use a solid material such as rubber with known ultrasonic properties. Neither of these QUS phantoms satisfactorily simulates bone morphometry. Accordingly, the interaction of the acoustic wave from the QUS device and the phantom do not mimic bone, resulting in simulations that may not be particularly accurate. Additionally, liquids such as water are not very attenuative, such that the QUS device operates at minimum power. The solid phantoms also have aging effects. For example, materials with good BUA characteristics are typically rubbery. One typical material used for QUS phantoms is neoprene. As the neoprene material ages, more cross-linking between the molecules in the material occurs. This cross-linking results in a harder material and changes in the acoustic properties. The change in material hardness thereby reduces the utility of the QUS phantom for long term monitoring. Moreover, the water and solid QUS phantoms both have temperature induced drift or value changes.

BRIEF DESCRIPTION OF THE INVENTION

In accordance with one embodiment, an electronic phantom for a quantitative ultrasound device is provided. The electronic phantom includes a housing, a first transducer element within the housing configured to receive an ultrasonic signal from a quantitative ultrasound device and a second transducer element within the housing connected to the first transducer element. The second transducer element is configured to transmit a modified ultrasonic sound wave to the quantitative ultrasound device based on the received ultrasonic signal. The first and second transducer elements are positioned in a back to back configuration within the housing.

In accordance with another embodiment, an electronic phantom for a quantitative ultrasound device is provided. The electronic phantom includes an input for receiving an ultrasonic signal from a quantitative ultrasound device and a signal modification module connected to the input. The signal modification module is configured to mimic one or more acoustic properties of a bone. The electronic phantom further includes an output connected to the signal modification module for transmitting a modified ultrasonic signal based on the mimicked acoustic property.

In accordance with yet another embodiment, a method for electronically mimicking a bone for use in phantom testing of a quantitative ultrasound device is provided. The method includes determining one or more acoustic properties of a bone to be mimicked and modulating a received ultrasonic signal from the quantitative ultrasound device based on the determined acoustic properties. The method further includes transmitting the modulated ultrasonic signal to the quantitative ultrasound device.

DETAILED DESCRIPTION OF THE INVENTION

Figure 1:
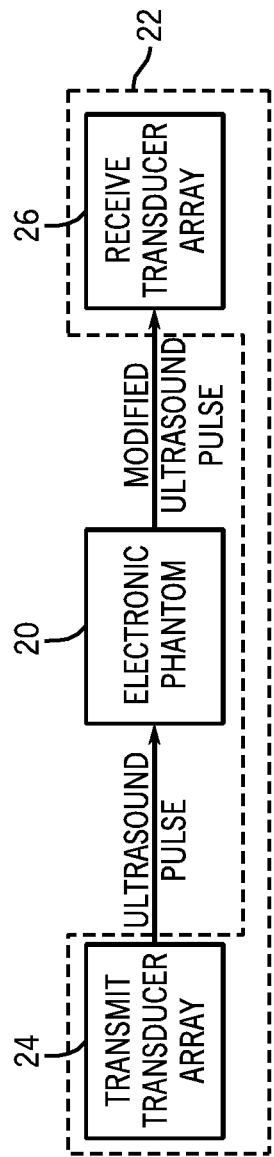
FIG. 1 is a simplified block diagram illustrating an electronic phantom constructed in accordance with various embodiments for use with a Quantitative Ultrasound (QUS) device.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. One or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Exemplary embodiments of an electronic phantom for use with a Quantitative Ultrasound (QUS) device, such as an ultrasound bone densitometer or ultrasonometer are described in detail below. Various embodiments provide an electronic device and/or electronic control of a phantom that allows for modifying an ultrasound pulse between an ultrasound transmitter and an ultrasound receiver of a QUS device. The electronic phantom mimics a bone with the electronics and also may allow for varying the bone quality or properties of the mimicked bone. The electronic phantom may be used in connection with any QUS device, for example, the Lunar Achillies ultrasonometer available from GE Healthcare or other ultrasound bone densitometer.

Specifically, as shown in FIG. 1, various embodiments of the invention provide an electronic phantom 20 that is configured to mimic the properties or characteristics of bone, for example, the acoustic properties of a human heel bone (also referred to as the calcaneus). The electronic phantom 20 may be used with a QUS device 22, for example, to validate or test the operation of the QUS device 22. In various embodiments, the QUS device 22 includes a transmit transducer array 24 and a receive transducer array 26 with the electronic phantom 20 provided therebetween. More particularly, the electronic phantom 20 is provided in an ultrasonic sound path between the transmit transducer array 24 and the receive transducer array 26. It should be noted that the transmit transducer array 24 and the receive transducer array 26 may include one or more transducer elements.

The transmission and reception of ultrasound pulses by the QUS device 22 are used to measure the physical properties of an object, for example, a bone of a human heel positioned between the transmit transducer array 24 and the receive transducer array 26. For example, the QUS device 22 is configured to measure the integrity and/or density of the object. In particular, the QUS device 22 can determine the physical properties and/or integrity of the object by comparing either relative transmit times (also referred to as time-of-flight or speed of sound) and/or relative broadband ultrasonic attenuation (BUA) through the object using the transmit transducer array 24 and the receive transducer array 26.

Accordingly, the electronic phantom 20 in various embodiments mimics certain characteristics or properties, such as acoustic properties, of bone by altering or modifying an ultrasonic signal, which may be one or more pulses transmitted from the transmit transducer array 24. As a result of the modification of the signal, the receive transducer array 26 receives a signal that is modified with respect to, for example, time-of-flight or BUA. Because the signal is modified using a known value, the QUS device 22 can be tested for accuracy or validated when compared to the known value. Thus, the electronic phantom 20 operates to modify the ultrasonic pulses used by the QUS device 22 to mimic a bone having a particular quality, characteristic or property, for example, a healthy bone or an osteoporotic bone. As an example, the time-of-flight or attenuation of an ultrasound pulse may be changed by modulating the ultrasound pulse as described in more detail herein to generate a modified ultrasonic sound wave. The modified ultrasonic sound wave allows for a determination of whether the QUS device 22 measured an expected value for a particular bone density or integrity that the electronic phantom 20 is mimicking.

Figure 2:
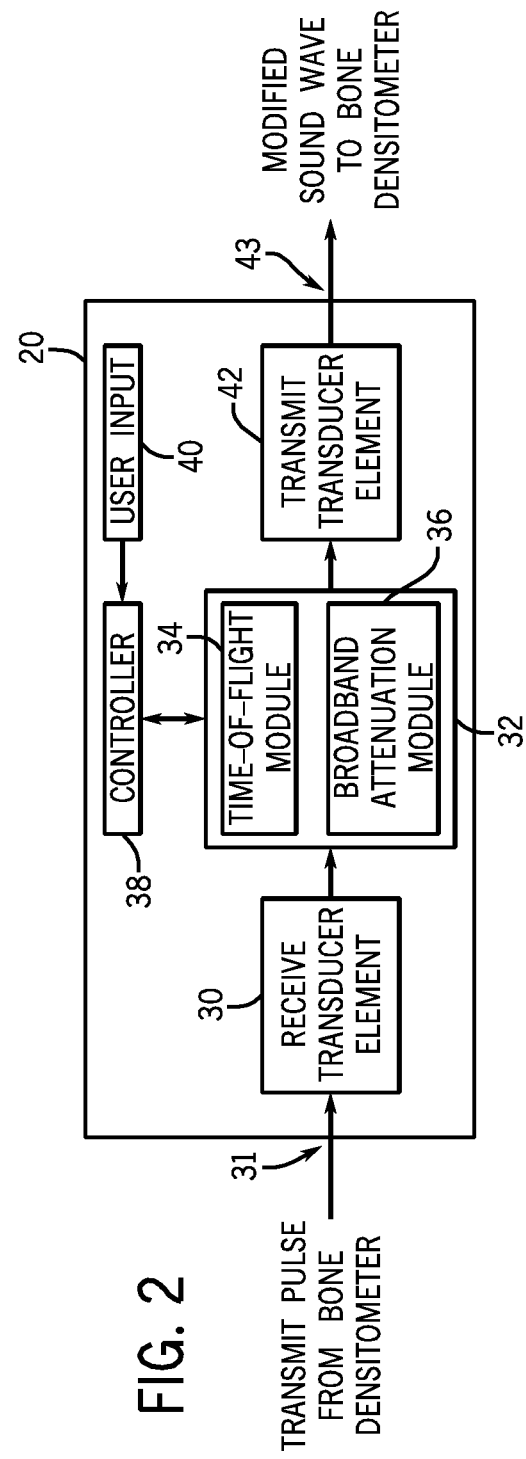
FIG. 2 is a block diagram of an electronic phantom constructed in accordance with various embodiments.

The electronic phantom 20 as shown in FIG. 2 includes a receive transducer element 30 at an input 31. For example, the receive transducer element 30 may include one or more transducers that are configured to receive ultrasonic signals. In particular, the receive transducer element 30 receives ultrasound pulses within the QUS device 22, and in particular, transmitted from the transmit transducer array 24 (shown in FIG. 1). The receive transducer element 30 is connected to a signal modification module 32 that modifies the received ultrasonic signal from the receive transducer element 30. For example, the signal modification module 32 changes a time of flight or BUA of the received ultrasonic signal using modulation and/or filtering techniques known in the art. In some embodiments, the signal modification module 32 includes a time-of-flight module 34 and a broadband attenuation module 36 that changes either the time-of-flight, namely the transit time or the BUA, respectively, of the received ultrasound signal. For example, the signal modification module 32 may be configured to operate as an active filter, such as a band-pass filter that only allows certain frequencies to pass through the electronic phantom 20. As another example, the signal modification module 32 may modulate received signals to attenuate the ultrasonic sound waves.

In some embodiments, the signal modification module 32 is optionally connected to a controller 38. The controller 38 is configured to adjust the modification of the signal, for example, the amount of signal modification, by adjusting the amount of time-of-flight change or BUA change to the received ultrasonic signal. For example, the controller 38 may be connected to a user input 40 that receives one or more control commands, such as a command from a user to select a particular bone type (e.g., osteoporotic bone) or acoustic property value that the electronic phantom 20 will mimic. The user may select a particular bone type from a predetermined list or may manually enter the exact signal modification characteristics that are desired or required, for example, to validate the QUS device 22, such as for use in osteoporosis testing.

The signal modification module 32 is also connected to a transmit transducer element 42 at an output 43. For example, the transmit transducer element 42 may include one or more transducers that are configured to receive the modified signal and communicate that signal as a modified ultrasonic sound wave. The transmit transducer element 42 outputs the modified signal and transmits the modified signal to the receive transducer array 26 (shown in FIG. 1). Thus, the electronic phantom 20 modifies ultrasonic pulses within a QUS device 22 to mimic a bone that has a particular characteristic or property that may define a particular bone condition. The electronic phantom 20 essentially includes a pair of transducer elements that are arranged in an opposite direction or configuration to the transducer arrays of the QUS device 22. Accordingly, the electronic phantom 20 mimics electronically the characteristics of, for example, a heel bone, and specifically, mimics a bone composition of the heel, which may be provided using active circuitry.

The electronic phantom 20 may include other elements or components. For example, a power supply (not shown) may be provided to power one or more components of the electronic phantom 20.

It should be noted that the electronic phantom 20 may be modified. For example, passive circuitry may be provided instead of active circuitry. As another example, the electronic phantom 20 may be modified such that the signal modification properties are fixed or predetermined and not adjustable as in the embodiment of FIG. 2.

Figure 3:
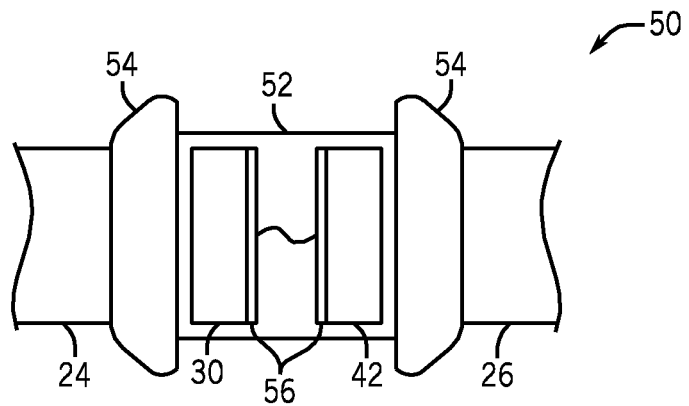
FIG. 3 is a pictorial illustration of an electronic phantom constructed in accordance with various embodiments.

In some embodiments, an electronic phantom 50 as shown in FIG. 3 is provided. It should be noted that like numerals represent like parts in the various embodiments. The electronic phantom 50 includes the receive transducer element 30 and the transmit transducer element 42 connected in a back to back configuration. In various embodiments, the receive transducer element 30 and the transmit transducer element 42 are connected in a parallel. The receive transducer element 30 is positioned in a housing 52 such that when placed within the QUS device 22, the receive transducer element 30 is positioned to receive signals from the transmit transducer array 24. Additionally, the transmit transducer element 42 is positioned in the housing 52 such that when placed within the QUS device 22, the transmit transducer element 42 is positioned to transmit signals to the receive transducer array 26. It should be noted that bladders 54, which may be inflatable and have therein an acoustic coupling fluid, may be provided such that the electronic phantom 50 is held in place within the QUS device 22 between the transmit transducer array 24 and the receive transducer array 26. Additionally, the acoustic coupling fluid therein may be temperature controlled.

It also should be noted that the housing 52 (e.g., glass casing) may be shaped and sized as desired or needed. For example, the housing 52 may be shaped and sized to fit within a particular QUS device 22. Additionally, the housing 52 may be shaped and sized such that the electronic phantom 50 fits within certain QUS devices 22, while not fitting within other QUS devices 22.

The electronic phantom 50 further includes a backing plate 56, for example, an aluminum backing plate coupled to a back of each of the receive transducer element 30 and the transmit transducer element 42. The backing plates 56 are configured to block acoustic signals.

The various components of the electronic phantom 50 may be provided to mimic a certain type of bone or certain properties of a bone, such as certain acoustic properties as described herein. In some embodiments, the electronic phantom 50 includes mismatched transducer elements, which may be lightly mismatched. For example, the electronic phantom 50 may include the following components formed in a layered stack:

1) The plate 56 configured as a thin (e.g., ⅛ inch) aluminum plate.
2) The receive transducer element 30 configured as a 500 kHz, 25 millimeter (mm) flat ultrasound transducer element.
3) An air gap.
4) The transmit transducer element 42 configured as a 480 kHz, 25 mm flat ultrasound transducer element.
5) The plate 56 configured as a thin (e.g., ⅛ inch) aluminum plate.

Figure 4:
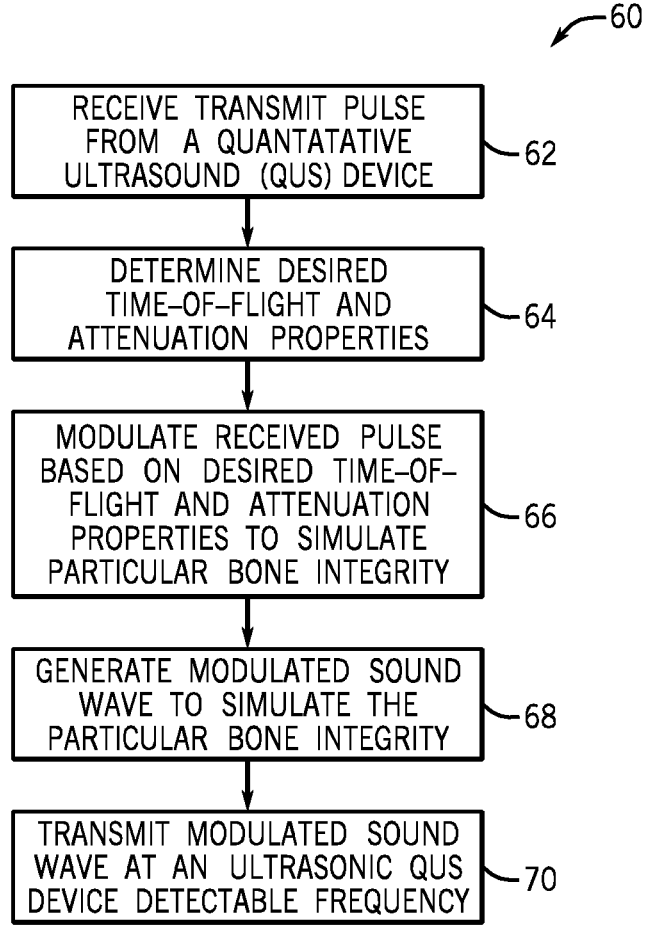
FIG. 4 is a flowchart of a method to electronically mimic a bone in accordance with various embodiments.
Figures 5, 6:
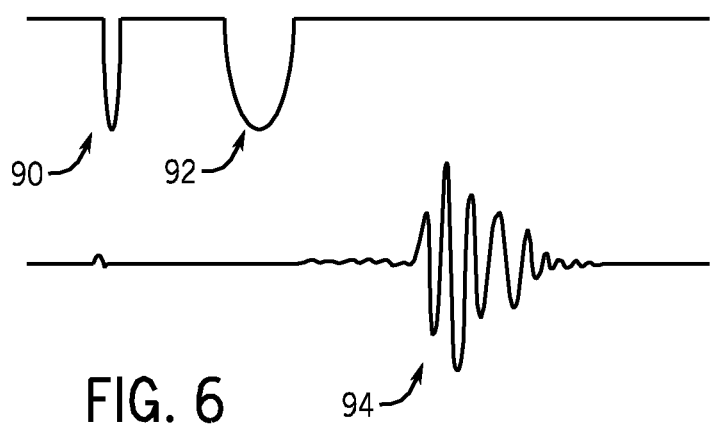
FIG. 5 is a table illustrating modulation characteristics for different simulate bone qualities used in accordance with various embodiments.
FIG. 6 is a signal diagram illustrating a modulated wave formed from an ultrasound pulse in accordance with various embodiments and a response from a QUS device.

According to various embodiments, a method 60 to electronically mimic a bone, for example, to operate as phantom in a QUS device to mimic a heel bone is shown in FIG. 4. The method 60 includes receiving a transmit pulse from a QUS device. For example, one or more pulses may be transmitted by the QUS device to an electronic phantom therein. The method then includes determining a desired acoustic property for the bone to be mimicked, which may include, for example, a time-of-flight and/or attenuation property (e.g., frequency attenuation property). In some embodiments, a user defined value or predetermined value may be used. In other embodiments, a table 80 as shown in FIG. 5 may be provided that is used to determine for each of a plurality of simulated bone qualities (shown in column 82), such as normal or osteoporotic for the electronic phantom, certain modulation characteristics corresponding to the particular acoustic properties. For example, for each simulated bone quality, a time-of-flight property (shown in column 84) and a BUA property (shown in column 86) are provided. For example, the properties may define a particular frequency attenuation or filtering to be used to adjust the received ultrasound pulse. For example, the modulation characteristics may define a time-of-flight profile or a BUA profile for use in modifying a received ultrasonic signal from a QUS device. In some embodiments, specific values are provided for each of the different modulation characteristics. Additionally, in some embodiments, the acoustic properties that are mimicked are set, for example, by the physical components of an electronic phantom such as by using mismatched transducer elements and are not adjustable.

It should be noted that each of the bone qualities and corresponding profiles or values in the table 80 may be stored in a database or matrix. The profiles or values may include absolute values based on, for example, time-of-flight times or BUA values using different factors such as an age, weight, height, race or sex of a type of individual for which a bone is to be mimicked.

Referring again to the method 60, thereafter the received pulse is modulated at 66 based on the determined acoustic properties, for example, desired time-of-flight and BUA properties, such as determined using the table 80. The identified properties simulate a particular bone type, condition or property. Thereafter, a modulated sound wave is generated at 68 to simulate or mimic the particular bone type, condition or property, for example, which may correspond to a particular bone integrity. The modulated sound wave is then transmitted at a QUS detectable frequency at 70. Thus, as shown in FIG. 6, a received signal 90 may be modified to produce a signal 92 having a different time-of-flight or BUA profile with a response 94 generated by the QUS device, which should correspond to the change to the received signal 92.

Figure 7:
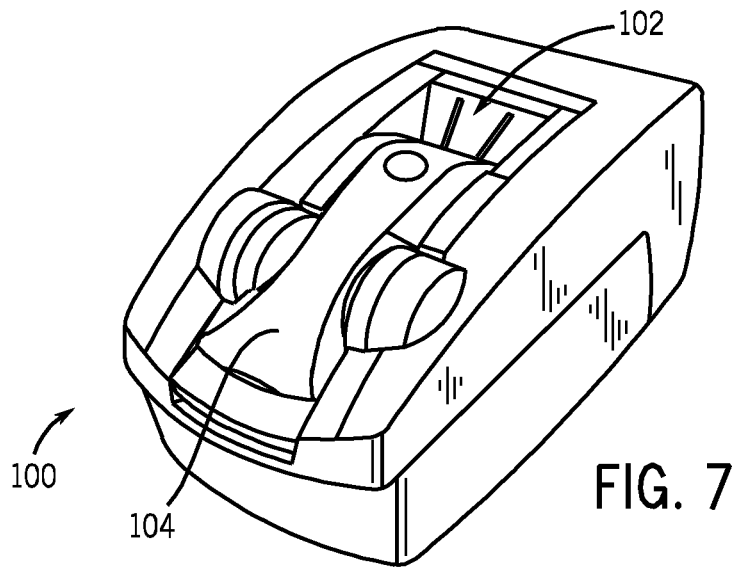
FIG. 7 is a perspective view of a QUS device in connection with which a phantom in accordance with various embodiments may be used.
Figure 8:
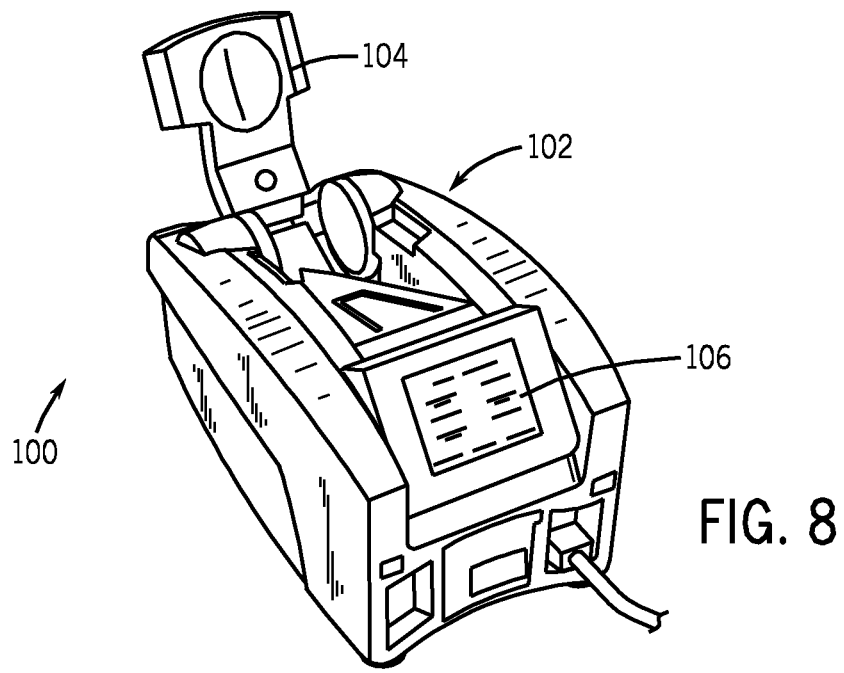
FIG. 8 is another perspective view of a QUS device in connection with which a phantom in accordance with various embodiments may be used.

The various embodiments may be used to provide an electronic phantom for use with any type of QUS device and to simulate different bones or portions of the body. For example, as shown in FIGS. 7 and 8 the QUS device may be an ultrasonometer 100 having a receiving portion 102 configured to receive therein a heel and a support member 104 for supporting a back of a leg. A display 106 also may be provided. The ultrasonometer 100 may be for example, an Achilles ultrasonometer with the various embodiments of phantoms described herein inserted within the receiving portion 102 and operating to modify ultrasound pulses transmitted therein to mimic a heel.

Thus, various embodiments of the invention provide an electronic phantom that simulates acoustic properties of bones, for example, using one or more time-of-flight and BUA values approximating, for example, a human heel bone. The simulated properties provide acoustic characteristics similar to bone. It should be noted that in some embodiments the simulated properties may be adjusted. In other embodiments, various types of bone quality may be simulated by selecting particular components, for example, selecting mismatched transducer elements.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An electronic phantom for a quantitative ultrasound device having a quantitative ultrasound transducer and a quantitative ultrasound receiver, the electronic phantom comprising:
a housing;
a first transducer element within the housing configured to receive an ultrasonic signal from the quantitative ultrasound transducer; and
a second transducer element within the housing connected to the first transducer element and configured to transmit a modified ultrasonic sound wave to the quantitative ultrasound receiver based on the received ultrasonic signal, wherein the first and second transducer elements are positioned in a back to back configuration within the housing;
wherein the first transducer and second transducer are positioned between the quantitative ultrasound transducer and the quantitative ultrasound receiver.

2. An electronic phantom in accordance with claim 1 wherein the first and second transducer elements are configured to generate an attenuated ultrasonic sound wave as the modified ultrasonic sound wave, wherein the attenuated ultrasonic sound wave corresponds to attenuation in a bone of a human heel.

3. An electronic phantom in accordance with claim 2 wherein the first and second transducer elements are configured to change one of a time-of-flight and a broadband ultrasound attenuation of the received ultrasonic signal to generate the modified ultrasonic sound wave.

4. An electronic phantom in accordance with claim 3 wherein the first and second transducer elements comprise mismatched transducers.

5. An electronic phantom in accordance with claim 4 wherein the mismatch is defined by a difference in operating frequency based on an attenuation characteristic of a heel bone.

6. An electronic phantom in accordance with claim 1 wherein the first and second transducer elements are connected in parallel.

7. An electronic phantom in accordance with claim 1 wherein at least one of a size and shape of the housing is configured to engage a determined type of quantitative ultrasound device.

8. An electronic phantom in accordance with claim 1 further comprising a signal modification module connected to the first and second transducer elements and configured to adjustably vary one of a time-of-flight and broadband ultrasound attenuation of the received ultrasonic signal to generate the modified ultrasonic sound wave.

9. An electronic phantom in accordance with claim 8 further comprising a controller connected to the signal modification module that receives a user input to control the generation of the modified ultrasonic sound wave.

10. An electronic phantom in accordance with claim 1 further comprising a metal backing layer coupled to a back of each of the first and second transducer elements.

11. An electronic phantom in accordance with claim 10 wherein the first and second transducer elements with the metal backing layers comprise a layered stack.

\* \* \* \* \*